United States Patent
Lin

(10) Patent No.: US 9,462,949 B2
(45) Date of Patent: Oct. 11, 2016

(54) METHOD FOR BIOMEDICAL SYSTEM

(71) Applicant: CHUNG HUA UNIVERSITY, Hsinchu (TW)

(72) Inventor: Jium Ming Lin, Hsinchu (TW)

(73) Assignee: CHUNG HUA UNIVERSITY, Hsinchu (TW)

( * ) Notice: Subject to any disclaimer, the term of this patent is extended or adjusted under 35 U.S.C. 154(b) by 73 days.

(21) Appl. No.: 14/448,184

(22) Filed: Jul. 31, 2014

(65) Prior Publication Data

US 2016/0029891 A1 Feb. 4, 2016

(51) Int. Cl.
| | |
|---|---|
| A61B 5/00 | (2006.01) |
| G08C 17/00 | (2006.01) |
| H04Q 9/00 | (2006.01) |
| A61B 5/053 | (2006.01) |
| A61B 5/11 | (2006.01) |
| A61N 5/00 | (2006.01) |

(52) U.S. Cl.
CPC ............. *A61B 5/0026* (2013.01); *A61B 5/002* (2013.01); *A61B 5/0532* (2013.01); *A61B 5/1113* (2013.01); *G08C 17/00* (2013.01); *H04Q 9/00* (2013.01); *A61N 5/00* (2013.01); *H04Q 2209/47* (2013.01)

(58) Field of Classification Search
CPC A61B 5/0532; A61B 5/6806; A61B 5/6807; A61B 5/7257; A61B 5/0022; A61B 2560/0425; A61B 2560/0431
See application file for complete search history.

(56) References Cited

U.S. PATENT DOCUMENTS

| | | | |
|---|---|---|---|
| 2005/0197555 A1* | 9/2005 | Mouradian | A61B 5/14532 600/365 |
| 2006/0139166 A1* | 6/2006 | Choutier | A61B 5/0002 340/539.12 |
| 2011/0009926 A1 | 1/2011 | Lin | |
| 2011/0199216 A1* | 8/2011 | Flinsenberg | A61B 5/1117 340/573.1 |
| 2012/0123291 A1* | 5/2012 | Lin | A61B 5/0532 600/548 |
| 2013/0317753 A1* | 11/2013 | Kamen | G06F 19/3412 702/19 |

FOREIGN PATENT DOCUMENTS

| | | |
|---|---|---|
| CN | 101425149 | 10/2010 |
| TW | 201102942 | 1/2011 |

OTHER PUBLICATIONS

Office Action and search report dated May 17, 2016 from the Taiwan counterpart application 103123413.
English abstract translation of the Office Action dated May 17, 2016 from the Taiwan counterpart application 103123413.
English abstract translation of TW 201102942.
English abstract translation of CN 101425149.
US publication 2011/0009926 is a counterpart of the cited TW201102942A.

* cited by examiner

*Primary Examiner* — Nabil Syed
(74) *Attorney, Agent, or Firm* — WPAT, P.C., Intellectual Property Attorneys; Anthony King

(57) ABSTRACT

A method used for a biomedical system is disclosed. The biomedical system includes an RFID apparatus and a reader apparatus communicating with the RFID apparatus. The RFID apparatus includes an electrode disposed adjacent to an acupuncture point and a motion monitor device including an accelerometer, a gyrocompass, or a pressure sensor. The method includes sending command information to the RFID apparatus from the reader apparatus; obtaining acupuncture impedance or bio-potential data through an electrode; providing nerve stimulation therapy by the RFID apparatus according to the command information, or using, by the RFID apparatus, the accelerometer, the gyrocompass, or the pressure sensor to obtain measurement data according to the command information; and submitting the acupuncture impedance/bio-potential data or the measurement data to the reader apparatus by the RFID apparatus.

10 Claims, 6 Drawing Sheets

METHOD FOR BIOMEDICAL SYSTEM

BACKGROUND

1. Technical Field

The present invention relates to a method for a biomedical system.

2. Related Art

In a hospital, patients may receive treatments and have examinations, or may take a walk around the hospital grounds. Therefore, patients may do various activities in hospitals. However, the systems currently used by hospitals cannot completely record all activities of patients, or instantly provide treatments according to conditions of the patients. Thus, the systems used by hospitals need improvements.

SUMMARY

In at least one embodiment, a method used for a biomedical system is disclosed. The biomedical system comprises an RFID apparatus and a reader apparatus configured to communicate with the RFID apparatus. The RFID apparatus comprises an electrode configured to be placed adjacent to an acupuncture point and a motion monitor device. The motion monitor comprises an accelerometer (e.g. a three axes type), a gyrocompass (e.g. a three axes type), or a pressure sensor. The method comprises sending command information to the RFID apparatus from the reader apparatus; obtaining, by the RFID apparatus, acupuncture impedance or bio-potential data through the electrode according to the command information; providing, by the RFID apparatus, nerve stimulation therapy through the electrode according to the command information, or using, by the RFID apparatus, the accelerometer, the gyrocompass, or the pressure sensor to obtain measurement data according to the command information; and submitting the acupuncture impedance, the bio-potential data, or the measurement data to the reader apparatus.

To better understand the above-described objectives, characteristics and advantages of the present invention, embodiments, with reference to the drawings, are provided for detailed explanations.

BRIEF DESCRIPTION OF THE DRAWINGS

The invention will be described according to the appended drawings in which.

DETAILED DESCRIPTION OF DISCLOSED EMBODIMENTS

The following description is presented to enable any person skilled in the art to make and use the disclosed embodiments, and is provided in the context of a particular application and its requirements. Various modifications to the disclosed embodiments will be readily apparent to those skilled in the art, and the general principles defined herein may be applied to other embodiments and applications without departing from the spirit and scope of the disclosed embodiments. Thus, the disclosed embodiments are not limited to the embodiments shown, but are to be accorded the widest scope consistent with the principles and features disclosed herein.

In some embodiments of the present invention, a method for a biomedical system is configured to monitor the activities of users. In some embodiments, a method for a biomedical system is configured to continuously monitor the activities of users. In some embodiments of the present invention, a method for a biomedical system is configured to provide treatments for users. In some embodiments of the present invention, a method for a biomedical system is configured to provide users with timely treatments. In some embodiments of the present invention, a method for a biomedical system is configured to monitor user activities and provide treatments. In some embodiments, a method for a biomedical system is configured to adjust treatments according to collected data. In some embodiments of the present invention, a method for a biomedical system is configured to measure acupuncture impedance or bio-potential data. In some embodiments of the present invention, a method for a biomedical system is configured to provide a nerve stimulation therapy. In some embodiments, a method for a biomedical system is configured to use an RFID (radio frequency identification) communication protocol; however, the present invention is not limited to such a communication protocol.

Figure 1:
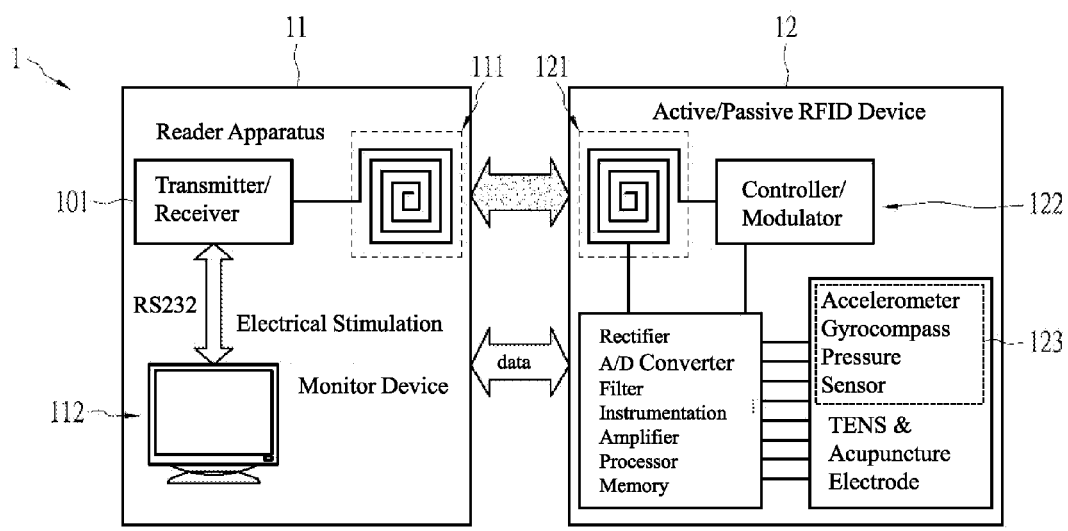
FIG. 1 is a view showing a biomedical system according to one embodiment of the present invention.

Referring to FIG. 1, in some embodiments, a biomedical system 1 comprises a reader apparatus 11 and an RFID apparatus or tag 12. The reader apparatus 11 can communicate with the RFID apparatus 12.

Referring to FIG. 1, the reader apparatus 11 comprises a transmitter/receiver 101. The transmitter/receiver 101 is coupled with an antenna 111 for transmitting data and/or electrical energy to the RFID apparatus 12 or receiving data from the RFID apparatus 12.

Referring to FIG. 1, the biomedical system 1 may comprise a monitor device 112, which can communicate with the transmitter/receiver 101. The monitor device 112 is configured to analyze data received by the transmitter/receiver 101 or provide required data for the transmitter/receiver 101 for transmission to the RFID apparatus 12. In one embodiment, after the monitor device 112 receives data from the RFID apparatus 12, the monitor device 112 displays an alert message. In one embodiment, the monitor device 112 communicates with the transmitter/receiver 101 by RS232 protocol; however, the present invention is not limited to such a protocol.

Referring to FIG. 1, in some embodiments, the RFID apparatus 12 is an active RFID device. In some embodiments, the RFID apparatus 12 is a passive RFID device. In some embodiments, the RFID apparatus 12 comprises an antenna 121, which is used to establish wireless communications with the reader apparatus 11. The RFID apparatus 12 may comprise a controller/modulator 122. The controller/modulator 122 can be coupled with the antenna 121. The controller/modulator 122 is configured to use modulating signals in order to vary carrier waves and extract information-embedded signals from modulated carrier waves.

Referring to FIG. 1, in some embodiments, the RFID apparatus 12 comprises a rectifier. The rectifier is configured to rectify radio signals received by the antenna 121 so as to generate power in direct currents (DC), whereby the RFID apparatus 12 is activated from sleep mode or passive mode to active mode and the system of the RFID apparatus 12 is initialized. After system initialization, the RFID apparatus 12 can use a back-up DC battery to drive itself.

In some embodiments, the RFID apparatus 12 comprises a motion monitor device 123. The motion monitor device 123 is configured to provide location information of the RFID apparatus 12.

Referring to FIG. 1, in some embodiments, the motion monitor device 123 comprises an accelerometer, which can be used to measure acceleration of the RFID apparatus 12.

Referring to FIG. 1, in some embodiments, the motion monitor device 123 comprises an electronic gyrocompass, which can be used to provide attitude or orientation or a movement direction of the RFID apparatus 12.

Referring to FIG. 1, in some embodiments, the motion monitor device 123 comprises a pressure sensor, which is used to provide altitude information of the RFID apparatus 12.

In some embodiments, the motion monitor device 123 comprises any two of the accelerometer, the electronic gyrocompass, and the pressure sensor. In some embodiments, the motion monitor device 123 comprises all the accelerometer, the electronic gyrocompass, and the pressure sensor.

Referring to FIG. 1, in some embodiments, the RFID apparatus 12 comprises an electrode (or a TENS (transcutaneous electrical nerve stimulation) and an acupuncture pad). The electrode is configured to measure acupuncture impedance or bio-potential data or to conduct a nerve stimulation therapy.

Referring to FIG. 1, in some embodiments, the RFID apparatus 12 comprises a processor and a memory. The memory stores required programs for the RFID apparatus 12 and the processor is configured to execute instructions of the programs.

Referring to FIG. 1, in some embodiments, the RFID apparatus 12 comprises an A/D (analogue/digital) converter. The A/D converter is configured to convert signals from the accelerometer and/or gyrocompass into digital signals, which are then sent to the processor.

Referring to FIG. 1, in some embodiments, the RFID apparatus 12 comprises an amplifier. The amplifier can amplify signals from the accelerometer. In one embodiment, the amplifier comprises an instrumentation amplifier.

Referring to FIG. 1, in some embodiments, the RFID apparatus 12 comprises a filter. The filter is configured to filter out some unwanted components (e.g. noise) from a signal. The signal may be related to the controller/modulator 122, the motion monitor device 123, or the electrode.

Figure 2A:
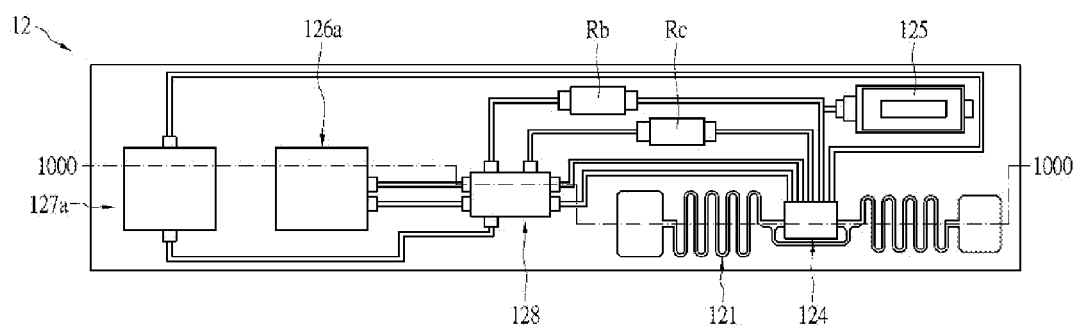
FIG. 2A is a view showing an RFID apparatus according to one embodiment of the present invention.
Figure 2B:
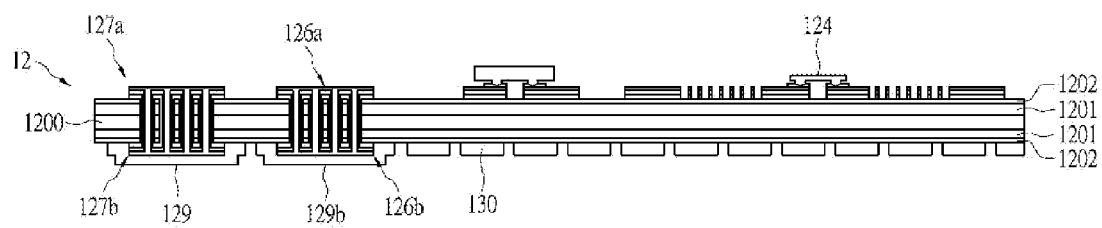
FIG. 2B is a cross-sectional view along line 1000-1000 of FIG. 2A.

Referring to FIGS. 2A and 2B, in some embodiments, the RFID apparatus 12 comprises a substrate 1200. The substrate 1200 is configured to support circuits or components of the RFID apparatus 12. The substrate 1200 can be flexible so as to make the RFID apparatus 12 flexible.

Referring to FIG. 2A, in some embodiments, two surfaces of the substrate 1200 are respectively disposed by vapor deposition with a silicon dioxide layer 1201 having a thickness of from 1 to 20 micrometers; however, the present invention is not limited to the afore-mentioned limits. A positive photoresist layer 1202 with a thickness of from 20 to 100 micrometers (however, the present invention is not limited to the afore-mentioned time limits) is formed on the silicon dioxide layer 1201 in order to protect the silicon dioxide layer 1201.

Referring to FIGS. 2A and 2B, in some embodiments, circuits are formed on the photoresist layer 1202. The circuits are used to connect the antenna 121, the RFID chip 124, resistors (Rb and Rc), a power source 125, a transistor driver, a buffer and amplifier circuit 128, conductive pads (126a, 126b, 127a, and 127b), an accelerometer, an electronic gyrocompass, and a pressure sensor. The transistor driver, such as a bipolar junction transistor (BJT) driver, is configured to be controlled, by the RFID chip 124, to adjust or amplify currents for performing transcutaneous electrical nerve and acupuncture point stimulation according to command information from the reader apparatus 11. In some embodiments, the circuits comprise chromium, nickel, and gold.

In one embodiment, two conductive pads (126a and 126b) or (127a and 127b) are connected by a conductive pillar through the substrate 1200.

In one embodiment, two conductive pads (127a and 127b) are used as ground electrodes, and another two conductive pads (126a and 126b) are used to measure acupuncture impedance or bio-potential data or to stimulate nerves.

In some embodiments, the RFID chip 124 includes the processor and the memory as shown in FIG. 1. In some embodiments, the RFID chip 124 includes the A/D converter, the filter, and the rectifier. The accelerometer, the electronic gyrocompass, and the pressure sensor can all be formed on the substrate 1200 as shown in FIG. 2B so as to reduce the size of the RFID apparatus 12.

Figure 3:
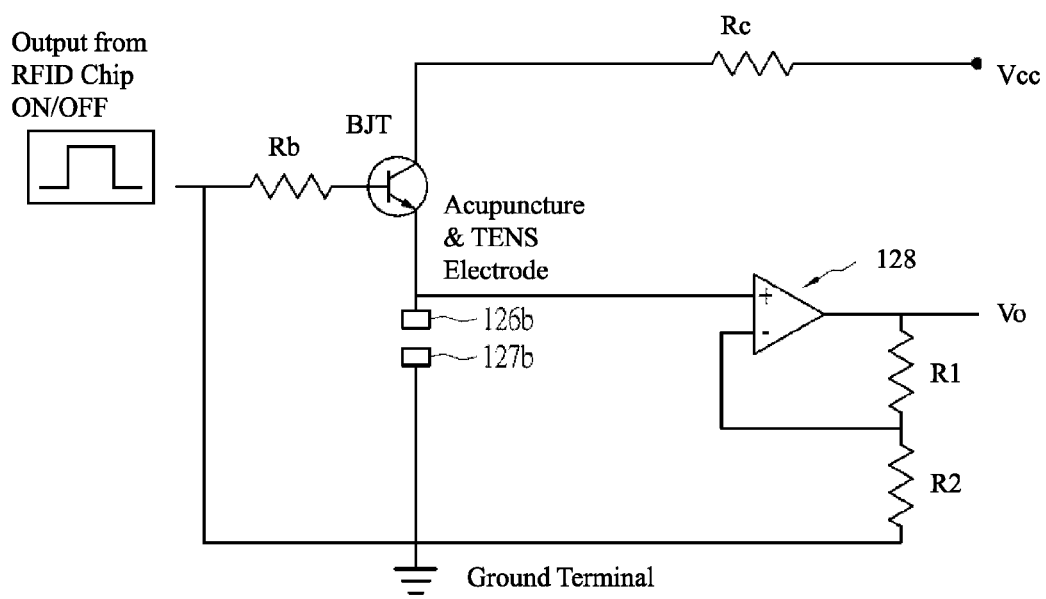
FIG. 3 is a diagram showing a transistor driver according to one embodiment of the present invention.

Referring to FIG. 3, the RFID apparatus 12 includes all components of FIG. 3. The emitter of the above-mentioned BJT driver is connected with a conductive pad 126b (or 126a), and another conductive pad 127b (or 127a) is grounded. The base electrode is connected with a terminal of the RFID chip 124 through a resistor Rb, and the collector is connected with a positive terminal of a power source through a resistor (Rc). In addition, an input of the buffer and amplifier circuit 128 is connected with a conductive pad 126b (or 126a) and another input of the buffer and amplifier circuit 128 is connected with a conductive pad 127b (or 127a).

Referring to FIG. 2B, in some embodiments, conductive patches 129 and 129b are attached to the bottom surfaces of the two conductive electrodes or pads (126b and 127b), and another portion under the substrate 1200 is attached with a double-sided non-conductive tape so that the RFID apparatus 12 can be attached to the human body, such as arms, legs, or the torso.

Figure 4:
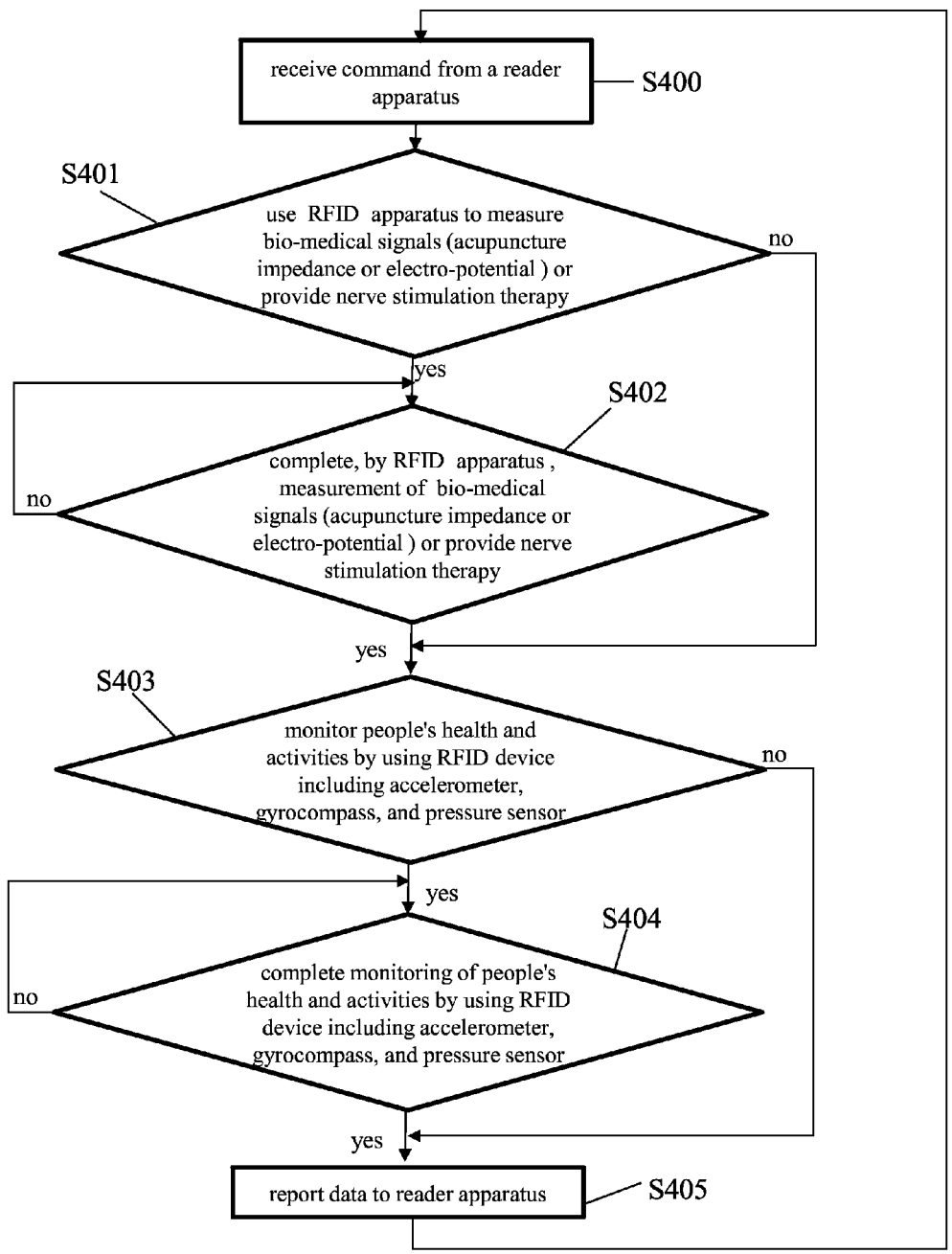
FIG. 4 is a flow chart related to a method for a biomedical system according to one embodiment of the present invention.

In some embodiments, the method for a biomedical system is configured to provide an RFID apparatus 12 for a user. In some embodiments, the user attaches the RFID apparatus 12 to his or her body, such as an arm, a leg, or the torso. In some embodiments, the user attaches the RFID apparatus 12 to his or her body and the RFID apparatus 12 covers an acupuncture point by the pad 129b. Referring to FIG. 4, the reader apparatus 11 of the biomedical system 1 provides command information for the RFID apparatus 12. In some embodiments, the reader apparatus 11 provides the same command information for multiple RFID apparatuses 12. In some embodiments, the reader apparatus 11 provides different command information for multiple RFID apparatuses 12.

In Step S400, the RFID apparatus 12 receives the command information from the reader apparatus 11. In Step S401, after the RFID apparatus 12 receives the command information, the RFID apparatus 12 decodes instructions of the command information and determines if a measurement of acupuncture impedance (or bio-potential data) and/or a nerves stimulation treatment should be carried out through the electrodes (126b and 127b). If the reader apparatus 11 instructs the RFID apparatus 12 to carry out a measurement of acupuncture impedance (or bio-potential data) and/or a nerves stimulation treatment, the process of the method proceeds to Step S402; if the reader apparatus 11 does not instruct the RFID apparatus 12 to carry out a measurement of acupuncture impedance (or bio-potential data) and/or a nerves stimulation treatment, the process proceeds to Step S403.

In Step S402, in some embodiments, the RFID apparatus 12 measures acupuncture impedance or bio-potential data according to the received command information. In some embodiments, the RFID apparatus 12 provides a nerve stimulation therapy according to the received command information. In some embodiments, the RFID apparatus 12 alternately carries out a measurement of acupuncture impedance (or bio-potential data) and a nerves stimulation treatment according to the received command information. After Step S402 is completed, the process proceeds to Step 403.

In Step S403, the RFID apparatus 12 determines whether it is instructed by the command information to monitor the health and motion activity of the user.

In Step S404, if the RFID apparatus 12 determines that it is instructed by the command information to monitor the health and motion activity of the user, then the RFID apparatus 12 uses the accelerometer, the gyrocompass, or the pressure sensor to produce measurement data. In some embodiments, the RFID apparatus 12 uses any two of the accelerometer, the gyrocompass, or the pressure sensor to produce measurement data. In some embodiments, the RFID apparatus 12 uses all the accelerometer, the gyrocompass, and the pressure sensor to produce measurement data.

In Step S405, the RFID apparatus 12 submits the measurement data to the reader apparatus 11, and the process proceeds to Step S400.

Figure 5:
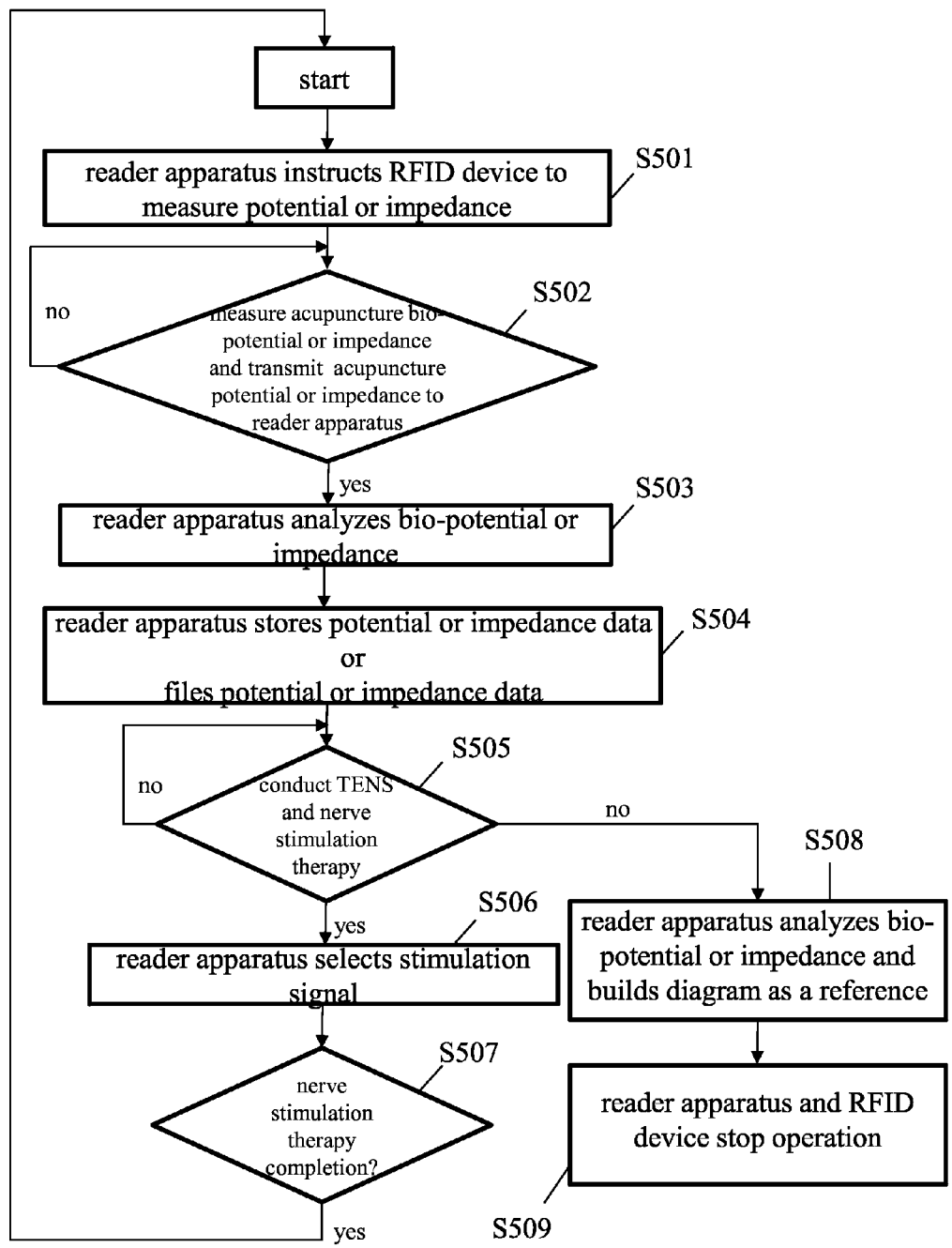
FIG. 5 is a flow chart related to a method for conducting a measurement of acupuncture impedance (or bio-potential data) and/or a nerves stimulation treatment according to one embodiment of the present invention.

Referring to FIG. 5, in Step S501, the reader apparatus 11 instructs the RFID apparatus 12 to measure acupuncture potential and/or impedance.

In Step S502, after the RFID apparatus 12 identifies the command information, which instructs it to measure acupuncture bio-potential and/or impedance, the RFID apparatus 12 measures acupuncture bio-potential and/or impedance and submits acupuncture bio-potential and/or impedance data to the reader apparatus 11.

In Step S503, the reader apparatus 11 analyzes the acupuncture bio-potential and/or impedance data.

In Step S504, the reader apparatus 11 stores or files the acupuncture bio-potential and/or impedance data.

In Steps S505, the reader apparatus 11 determines whether a nerve stimulation therapy or a nerves stimulation treatment is needed according to the acupuncture bio-potential and/or impedance data and previously filed data.

In Steps S506, the reader apparatus 11 selects a code of stimulating signal program, includes it in command information, and sends the command information to the RFID apparatus 12.

In Step S507, when the RFID apparatus 12 confirms receiving the code of stimulating signal program, the RFID apparatus 12 outputs stimulating signals to stimulate a corresponding acupuncture point according to the program.

In Step S508, when the reader apparatus 11 decides that a nerve stimulation therapy is no longer required, the reader apparatus 11 starts to analyze the acupuncture bio-potential and/or impedance data and use it to generate a diagram or curve for health condition analyses.

In Step S509, the reader apparatus 11 and the RFID apparatus 12 are halted.

Figure 6:
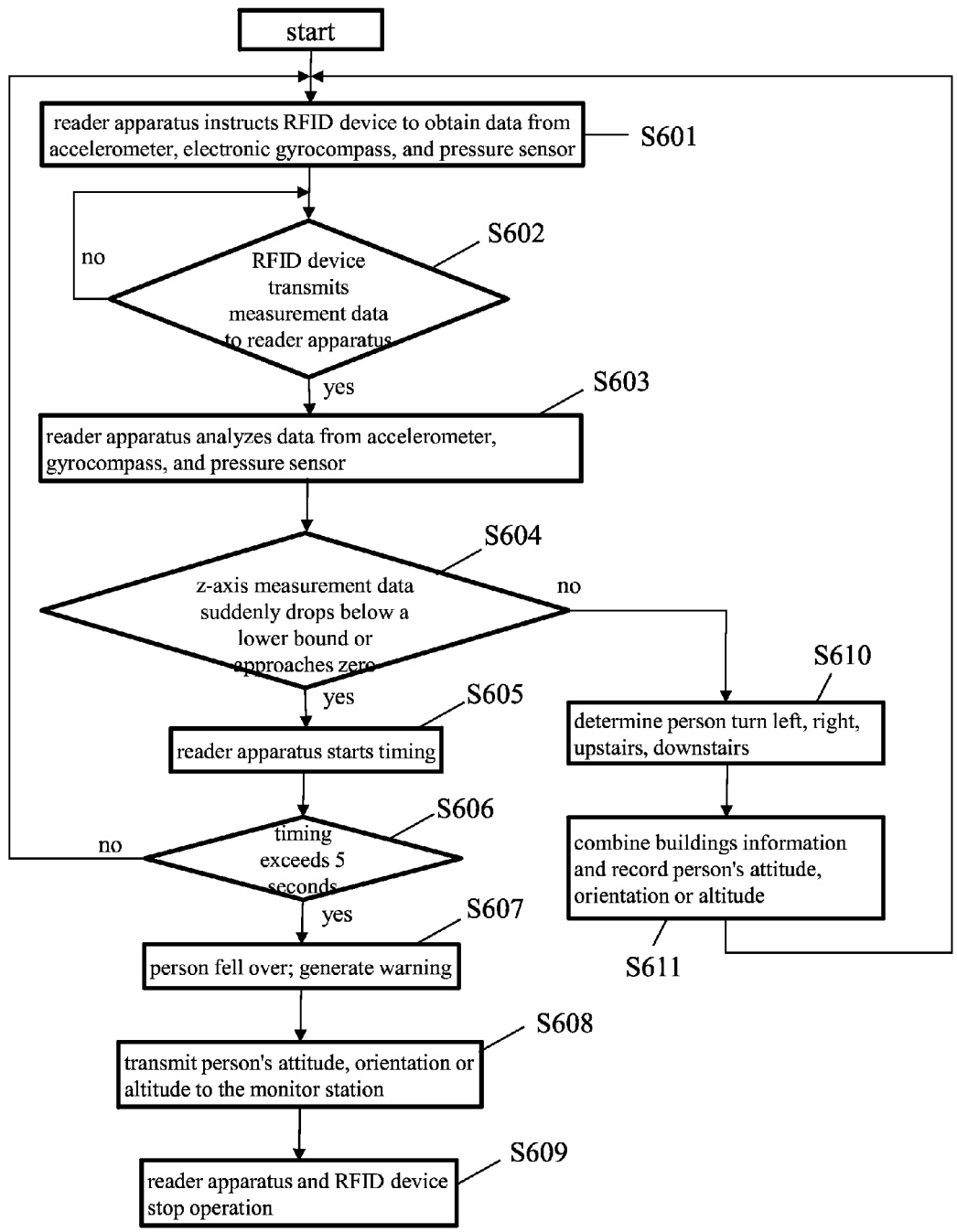
FIG. 6 is a flow chart related to a method of monitoring the health and activity of a person according to one embodiment of the present invention.

Referring to FIG. 6, in Step S601, the reader apparatus 11 instructs the RFID apparatus 12 to use the accelerometer, the gyrocompass, or the pressure sensor to produce measurement data for motion activity analyses.

In Step S602, after the RFID apparatus 12 confirms that command information instructs it to monitor the health and motion activity of the user, the RFID apparatus 12 uses the accelerometer, the gyrocompass, or the pressure sensor to produce measurement data, and then sends the measurement data to the reader apparatus 11.

In Step S603, the reader apparatus 11 analyzes the returned measurement data of motion activity from the accelerometer, the gyrocompass, or the pressure sensor.

In Step S604, the reader apparatus 11 determines whether the vertical acceleration value (along the Z-axis) in the measurement data suddenly drops below a lower bound (e.g. 0.3G, 1G=9.8 m/s$^2$) or approaches zero.

In Step S605, if the vertical acceleration value (along the Z-axis) in the measurement data suddenly drops below a lower bound (e.g. 0.3G, 1G=9.8 m/s$^2$) or approaches zero, the reader apparatus 11 starts timing.

In Step S606, the reader apparatus 11 determines whether the timing exceeds a limit. In some embodiments, the reader apparatus 11 determines whether the timing exceeds 5 seconds; however, the present invention is not limited to the afore-mentioned time limit.

In Step S607, when the timing exceeds the limit, the reader apparatus 11 issues an alarm signal.

In Step S608, when the timing exceeds the limit, the reader apparatus 11 provides the user's latest recorded location data within or outside of the building.

In Step S609, the reader apparatus 11 and the RFID apparatus 12 stop the process of operation after an alarm signal is issued.

In Step S610, when the vertical acceleration value (along the Z-axis) in the measurement data does not drop or is greater than a threshold (e.g. 0.9G), the reader apparatus 11 determines location information according to the measurement data. In some embodiments, the reader apparatus 11 determines a movement direction, attitude or orientation of the user according to the measurement data. In some embodiments, the reader apparatus 11 determines whether the user turned left, turned right, went upstairs or downstairs, and accordingly determines a new location of the user.

In Step S611, the reader apparatus 11 uses a building's information system and the measurement data to determine where and which floor the user is located. In one embodiment, the reader apparatus 11 comprises the building's information system.

In at least one embodiment, the biomedical system can completely records all activities of users and/or provide treatments according to the conditions of the users. Therefore, the system can improve medical quality.

It will be apparent to those skilled in the art that various modifications and variations can be made to the disclosed embodiments. It is intended that the specification and examples be considered as exemplary only, with a true scope of the disclosure being indicated by the following claims and their equivalent.

What is claimed is:

1. A method used for a biomedical system, the biomedical system comprising an RFID apparatus and a reader apparatus configured to communicate with the RFID apparatus, the RFID apparatus comprising electrodes configured to be placed adjacent to an acupuncture point and a motion monitor device, the motion monitor comprising a three-axes accelerometer, a three-axes gyrocompass, or a pressure sensor, the method comprising:

sending command information to the RFID apparatus from the reader apparatus;

determining, based on the command information, which operation between a first operation and a second operation is requested to be performed, wherein the first operation includes obtaining, by the RFID apparatus, acupuncture impedance or bio-potential data through the electrodes; and wherein the second operation includes using, by the RFID apparatus, the accelerometer, the gyrocompass, or the pressure sensor to obtain measurement data;

performing at least one of the first operation and the second operation according to the determination result;

submitting the acupuncture impedance or the bio-potential data to the reader apparatus either when the first operation is performed, or when the first operation and the second operation are performed; and submitting the measurement data to the reader apparatus either when the second operation is performed, or when the first operation and the second operation are performed.

2. The method of claim 1, further comprising a step of starting timing, by the reader apparatus, when the measurement data indicates that a vertical acceleration value approaches zero or below a lower bound.

3. The method of claim 2, further comprising a step of providing an alarm signal when the timing exceeds a limit.

4. The method of claim 2, further comprising a step of providing, by the reader apparatus, latest recorded location data when the measurement data indicates that a vertical acceleration value approaches zero or below a lower bound.

5. The method of claim 1, further comprising a step of determining, by the reader apparatus, location information according to the measurement data when the measurement data indicates that a vertical acceleration value is greater than a threshold.

6. The method of claim 1, wherein the reader apparatus comprises a building's information system.

7. The method of claim 1, further comprising a step of determining, by the reader apparatus, a movement direction, attitude or orientation of the RFID apparatus according to the measurement data.

8. The method of claim 1, further comprising a step of providing, by the reader apparatus, an instruction for conducting nerve stimulation therapy for the RFID apparatus according to the acupuncture impedance or bio-potential data.

9. The method of claim 1, further comprising a step of generating, by the reader apparatus, a diagram according to the acupuncture impedance or bio-potential data.

10. The method of claim 1, wherein performing the at least one of the first operation and the second operation according to the determination result includes performing one of the first operation and the second operation according to the determination result.

* * * * *